United States Patent
Igarashi et al.

[11] Patent Number: 6,141,602
[45] Date of Patent: Oct. 31, 2000

[54] SPECIMEN PROCESSING SYSTEM

[75] Inventors: Yoshiaki Igarashi, Mito; Mikio Komata, Hitachinaka, both of Japan

[73] Assignee: Hitachi, Ltd., Tokyo, Japan

[21] Appl. No.: 09/159,656

[22] Filed: Sep. 24, 1998

[30] Foreign Application Priority Data

Sep. 25, 1997 [JP] Japan ................................. 9-260367

[51] Int. Cl.⁷ ................................................. G06F 7/00
[52] U.S. Cl. .................. 700/226; 700/225; 422/104; 422/67
[58] Field of Search .................. 700/226, 225, 700/229, 230; 422/102, 104, 67

[56] References Cited

U.S. PATENT DOCUMENTS

| | | | |
|---|---|---|---|
| 4,751,186 | 6/1988 | Baisch et al. | 422/67 |
| 5,128,105 | 7/1992 | Berthold et al. | 422/102 |
| 5,150,795 | 9/1992 | Nakayama et al. | 209/3.3 |
| 5,366,062 | 11/1994 | Markin et al. | |
| 5,427,743 | 6/1995 | Makin | 422/104 |
| 5,623,415 | 4/1997 | O'Bryan et al. | 364/478.13 |
| 5,651,941 | 7/1997 | Stark et al. | 422/104 |
| 5,663,545 | 9/1997 | Marquiss | 422/104 |
| 5,700,429 | 12/1997 | Buhler et al. | 422/104 |
| 5,735,387 | 4/1998 | Polaniec et al. | 198/690.1 |
| 6,060,022 | 5/2000 | Pang et al. | 422/67 |

OTHER PUBLICATIONS

Hitachi Review, vol. 41, No. 4, 1992, "Total Clinical Laboratory Testing System for Laboratory Automation", T. Ikeda et al, pp. 167–172.

Clinical Inspection, vol. 37, No. 11, 1993 extra edition, "1 Specimen Transportation System—Philosophy of Development", Toshiba Medical Corp., Y. Suwa.

*Primary Examiner*—Christopher P. Ellis
*Assistant Examiner*—Khoi H. Tran
*Attorney, Agent, or Firm*—Mattingly, Stanger & Malur, P.C.

[57] ABSTRACT

When processing a specimen by a plurality of specimen processing devices arranged along a transportation line, a specimen tag on which a coded group code representing a combination including at least one processing item is adhered on the specimen container. A plurality of such specimen containers are mounted on a specimen support bearing a specific carrier tag. Prior to transporting the specimen support, the specimen tags and the carrier tag are read, and based on the read result, an information management and controlling unit and the respective specimen processing devices manage a corresponding relationship between the carrier tag and the group codes. At the respective specimen processing devices the specimen support is identified and the processing corresponding to the group code is performed for the respective concerned specimen.

5 Claims, 3 Drawing Sheets

SPECIMEN PROCESSING SYSTEM

BACKGROUND OF THE INVENTION

1. Field of the Invention

The present invention relates to a specimen processing system, more specifically, to a specimen processing system using specimen carriers for clinical inspections which is suitable for performing automatic specimen inspections.

2. Conventional Art

A usual specimen processing system includes a variety of processing units (such as a centrifugal separator, a plug or cap opener, a pipetter or aliquoter, a bar code labeler, a plug closer or a restopper, a sorter and an analyzer) each incorporating a rack transportation portion and transportation lines connecting these processing units, and through series connection of one processing unit with another processing unit, a transportation line with a processing unit and one transportation line with another transportation line the specimen processing system is constituted.

"Hitachi Review, vol. 41(1992), No. 4, pp 167—172" discloses an automatic specimen or sample handling system in which a transportation line for transporting specimens or samples is constituted by a plurality of transportation routes to branch the same into a plurality lines so as to permit distribution of a specimen into a variety of the processing units.

The processing units arranged in this system includes such as an automated centrifuge unit for separating blood into serums and cells, a cap opener unit for automatically removing the caps on the same sample containers, a pipetter or aliquoter unit for pipetting serums of a mother sample container to a daughter sample container, a bar code labeler unit for adhering a bar code label having the same ID as that of the mother sample on the daughter sample container, a plug closer or restopper unit for closing a sample container with a cap, a sample sorting unit for sorting the sample containers according to inspection groups and a chemical analyzer unit for performing an automatic chemical analysis on the samples.

"Clinical Inspection, vol. 37, No. 11 (1993, an extra edition)" discloses a provision of respective bar code readers for a plurality of functional units disposed in a specimen transportation system, thereby misidentification between specimens is prevented by reading bar code information attached on the respective specimen containers by the bar code readers.

U.S. Pat. No. 5,366,062 discloses a conveyer system for transporting specimen carriers each carrying specimen containers to a plurality of work stations.

In the conventional specimen processing systems as explained above, each of the specimen processing units performs the communication processing inquiring the processing items for every specimen container to a central information processing unit or a central controller, therefore, as the number of the specimen containers and the specimen processing units or devices increases, the amount of communication increases which necessitates a complex communication system of a large scale and a high processing speed.

SUMMARY OF THE INVENTION

An object of the present invention is to provide a specimen processing system in which even when the number of specimens to be processed and of specimen processing units increases, complexity and scale increase of the communication system between an information processing unit or a central controller which manages and controls the entirety of the specimen processing system and respective specimen processing units are suppressed.

A specimen processing system according to the present invention is provided with a specimen carrier carrying specimen containers each being capable of containing specimen, a transportation line for transportating the specimen carrier and a plurality of specimen processing devices arranged along the transportation line.

The specimen processing system is further provided with specimen tags each attached on the outer wall of the respective specimen containers and including a code representing specimen number and a group code representing grouped combinations of processing items performed by at least one of the plurality of specimen processing devices for the specimen contained in the concerned specimen container, identifiably coded carrier tags formed on the specimen carrier, a specimen tag reader for reading the specimen tags prior to transporting the specimen carrier toward the plurality of specimen processing devices, a first carrier tag reader for reading the carrier tag prior to transporting the specimen carrier toward the plurality of specimen processing devices, second carrier tag readers arranged for each of the plurality of specimen processing devices, processing device controllers each forming a pair with each of the respective specimen processing devices and for receiving information read from the concerned second carrier tag reader, and an information managing and controlling unit which registers corresponding relationship between the carrier tag and the group code for individual specimen carriers based on the read results of the specimen tags by the specimen tag reader and of the carrier tags by the first carrier tag reader, wherein each of the processing device controllers receives the registered corresponding relationship from the information managing and controlling unit and manages the carrier tag relating to the specimen processing device which forms a pair with the concerned processing device controller.

Each of the specimen processing devices in the specimen processing system, when carrier tag read by the concerned second carrier tag reader contains the group code corresponding to the processing items concerned to the specimen processing device, performs the processing of concerned processing items for the specimen container or the specimen on the specimen carrier bearing the read carrier tag.

According to one preferable embodiment of the present invention, when a processing item is included which does not correspond to any of preset groups among specimen tags read by the specimen tag reader, the information managing and controlling unit sets an inquiry request command to a specific processing device controller of a concerned specific specimen processing device which is determined to perform the processing of the non corresponding processing items. Thereafter, when the specific processing device controller recognizes the concerned carrier tag having the corresponding relationship with the non corresponding processing items, the specific processing device controller inquires processing information to the information managing and controlling unit and controls based on the processing information received from the information managing and controlling unit the concerned specific specimen processing device so as to perform the non corresponding processing items.

According to a further preferable embodiment of the present invention, the specimen processing system is further provided with a specimen distributing device in which, after reading tags with the specimen tag reader and the first carrier tag reader, a plurality of specimen containers bearing a same group code are mounted on a common specimen carrier and a specimen carrier completing the mounting of the plurality of specimen containers is supplied to the transportation line.

DESCRIPTION OF THE PREFERRED EMBODIMENTS

Figure 1:
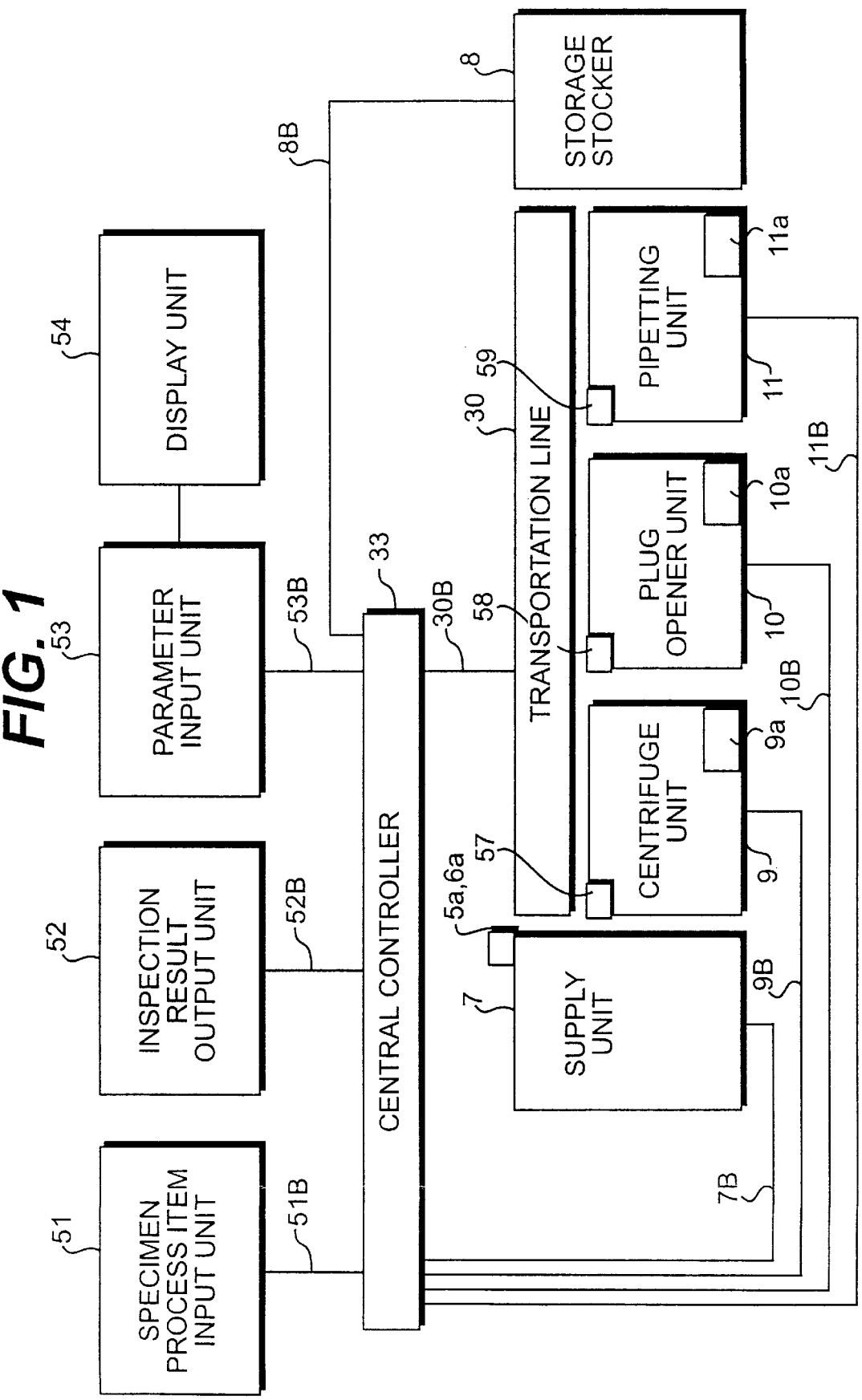
FIG. 1 is a block diagram of a specimen processing system according to the present invention in which a small number of specimen processing devices are disposed.

FIG. 1 shows a block diagram showing a constitution of one embodiment according to the present embodiment. In FIG. 1, specimens such as blood and urine are arranged on a rack supply unit 7 under a condition being held on a specimen rack functioning as a specimen carrier. Required processing items to be performed for respective specimens are entered into a specimen processing item input unit 51. An operator inputs for every specimen a processing item, a specimen ID (specimen identification information) for identifying respective specimens, and specimen attribute information (such as sampled date, sex and age of patient).

As processing items for respective specimens, such functions as a centrifugal separation, plug opening, specimen pipetting, specimen analysis, plug closing and temporary standing-by, which are provided for the specimen processing devices in the specimen processing system, are selected. Further, the processing items to be inputted includes specimen volume when pipetting the specimen with a pipetting device and analysis items to be inspected at the concerned analysis device.

In the central controller 33 which functions as an information managing and controlling unit, group codes for specimen processing with the specimen processing system are set in advance. In this instance, among the processing functions which are assigned to each of a specimen processing devices in the specimen processing system, every combination including at least one processing item having a high frequency to be designated for processing is grouped. For example, groups such as a combination of centrifugal separation, plug opening and pipetting, a combination of centrifugal separation and analysis, and a combination of pipetting and analysis are formed, and an identifiable group code is assigned for each of the groups and is registered in a memory of the central controller 33.

The central controller 33 controls a bar code label issue machine (not shown) so as to issue concerned bar codes for respective specimens to be subjected to concerned group processings. On the issued bar code label, specimen ID, specimen attribute information and group code relating to the specimen processing are indicated, further, when there are other processing items than those of the preset groups, a coded information instructing inquiry to the central controller 33 is indicated. On the respective specimen containers each containing a specimen, respective issued bar code labels functioning as specimen tags are adhered.

Other processing items than those of the preset groups, for example, analysis items and specimen pipetting volume are not indicated on the bar code labels, but are managed by the central controller 33 while correlating the other processing items than the grouped ones with the specimen ID and carrier ID. These managements supplement a shortage of indication capacity by the respective bar code labels.

Figure 2:
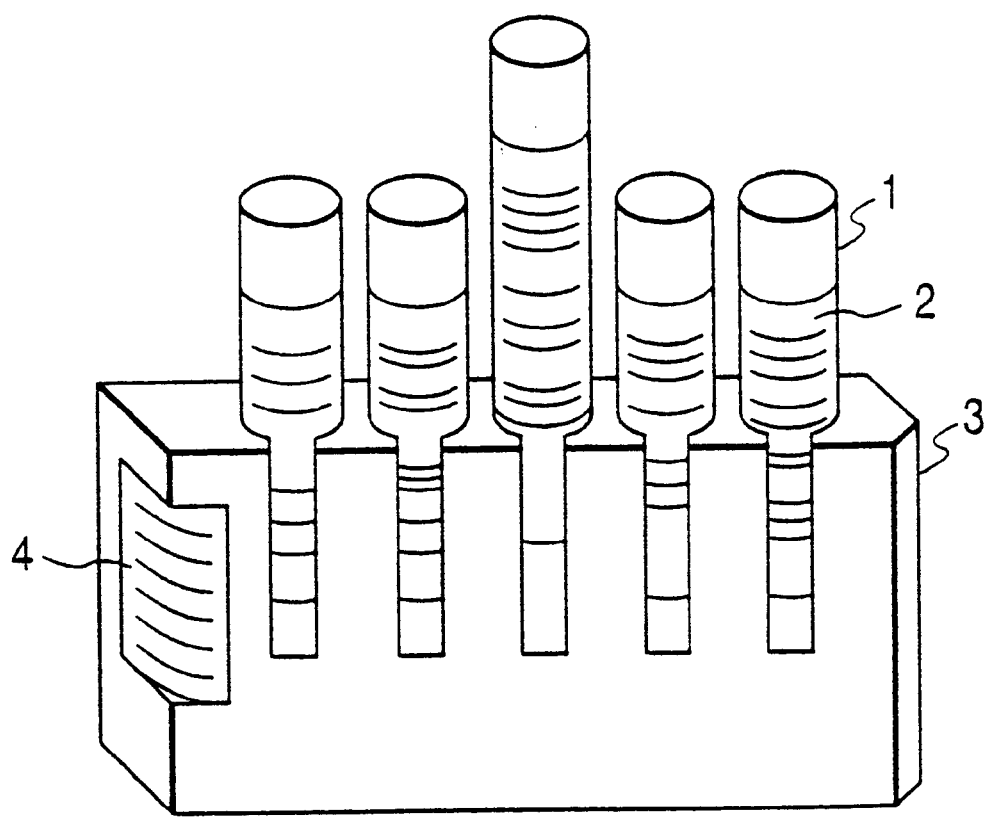
FIG. 2 is a view showing an example of specimen carriers used in the embodiment.

FIG. 2 shows a specimen carrier 3 on which specimen containers are mounted. The specimen carrier 3 is a box shaped member and can hold a plurality of specimen containers 1, for example, five specimen containers 1. On each of the specimen containers 1 a bar code label 2 functioning as a specimen tag as explained above is adhered. On a predetermined portion of the specimen carrier 3 a carrier tag 4 in a form of coded carrier number (carrier ID) is formed. In the example shown in FIG. 2, the carrier tag 4 is constituted by a bar code label, however, alternatively a plurality of light passing holes or slits which constitute binary codes can be formed as carrier tags.

In FIG. 1, an inspection result output unit 52 outputs result of requested inspection for respective specimen. On the rack supply unit 7 a plurality of specimen racks to be supplied to the respective specimen processing units can be placed and in accordance with the progress of processings of the specimen at respective specimen processing units the specimen racks 3 are supplied toward a transportation line 30 in the order of arrangement thereof in the supply unit 7.

The specimen rack 3 is transported from one place to another through driving a belt conveyer on the transportation line 30 by a pulse motor of a driving source. A rack storage stocker 8 stores the specimen racks 3 of which processing according to the request has been completed. A user of the system can take out a processing completed specimen rack 3 from the storage stocker 8. Specimen processing units 9, 10 and 11 are respectively assigned one of variety of specimen processing functions such as centrifugal separation, plug opening, pipetting, bar code label adhering, plug closing, sorting and analysis, and therefore, the size thereof varies. The respective specimen processing units introduce specimen racks 3 transported by the transportation line 30 thereinto through respective rack transfer mechanisms, and return the specimen racks 3 again to the transportation line 30 after completing the concerned processing.

An inlet receiving a specimen rack 3 from the transportation line 30 in the respective specimen processing units is an access position at the receiving side, and the outlet sending out the specimen rack 3 to the transportation line 30 in the respective specimen processing units is an access position at the discharging side. Such transfer between the transportation line 30 and the respective specimen processing units from one to another is performed through the rack transfer mechanisms. Therefore, the sending out position and the receiving position of the specimen rack 3 on the transportation line 30 correspond to the access positions for the specimen rack 3 in the respective specimen processing units, and respective rack transfer and mounting stations are formed by these positions and the rack transfer and mounting mechanisms.

The supply unit 7, the transportation line 30 and the storage stocker 8 are respectively connected to the central controller 33 via communication cables 7B, 30B and 8B, and the operation thereof is controlled by the central controller 33. Further, the specimen processing unit 9 operating as a centrifugal separator incorporates a unit controller 9a, the specimen processing unit 10 operating as a plug opener unit incorporates a unit controller 10a, and the specimen processing unit 11 operating as a pipetting unit incorporates a unit controller 11a. These unit controllers 9a, 10a and 11a are connected to the central controller 33 via respective cables 9B, 10B and 11B, and information is exchanged between the respective controllers.

The central controller 33 is connected to the specimen processing item input unit 51, the inspection result output unit 52 and a parameter input unit 53 via communication cables 51B, 52B and 53B. The central controller 33 causes to transfer a specimen rack 3 from the supply unit 7 to the transportation line 30 as well as to transfer a specimen from the transportation line 30 to the respective specimen processing units or the storage stocker 8 based on the request contents inputted from the specimen processing item input unit 51, and the storage stocker 8 stores the specimen racks 3 which were transferred via the transportation line 30 from the respective specimen processing units 9, 10 and 11. The respective unit controllers 9a, 10a and 11a forming pairs with the respective specimen processing units operate independently.

The parameter input unit 53 is what an operator inputs such parameters as type and position of the respective specimen processing units, timings when the respective specimen processing units send out the specimen rack 3 to another specimen processing unit or the storage stocker 8 via the transportation line 30 and type of specimen rack 3 to be handled. An image display unit 54 is connected to the central controller 30 so as to image-display a variety of information.

The rack supply unit 7 is provided with a reader unit 5a for reading information of the specimen tag 2 and a reader unit 6a for reading information of the carrier tag 4 near the outlet of the specimen racks 3. Carrier tag reader units 57, 58 and 59 for the respective processing units are disposed for the corresponding specimen processing units 9, 10 and 11.

In the system shown in FIG. 1, before transporting a specimen rack 3 from the supply unit 7 toward the specimen processing units 9, 10 and 11 via the transportation line 30, the carrier tag 4 of the specimen rack 3 is read by the carrier tag reader unit 6a, and further, the specimen tags 2 of the respective specimen containers 1 carried on the specimen rack 3 is read by the specimen tag reader unit 5a. Based on the read results, the central controller 33 registers the corresponding relationship between the carrier tags and the group codes with regard to individual specimen racks 3 of which information is read as well as transmits the information of the corresponding relationship to all of the concerned unit controllers forming pairs with the specimen processing units which can perform the respective processing functions contained in the group codes as combinations of processing items. The group codes in this instance are identifiable codes which are assigned to the respective groups consisting of combinations including at least one processing item which are preset in advance at the central controller 33.

The respective unit controllers which received information of such corresponding relationships register the carrier tag of the relating specimen processing unit forming a pair with the concerned unit controller, and manage the concerned carrier tag in preparation for the transportation of the concerned specimen rack 3. When a specimen rack 3 is transported to one of the specimen processing units via the transportation line 30, the carrier tag reader units 57, 58 and 59 for the concerned specimen processing units transmit the read information of the carrier tag to the concerned unit controller 9a, 10a or 11a. When the read information of the carrier tag contains the group code corresponding to the processing item of the concerned specimen processing unit, the concerned specimen processing unit is controlled to perform the predetermined processing item for the specimen containers or the specimens carried on the concerned specimen rack 3. Namely, one of the specimen processing units 9, 10 and 11 performs centrifugal separation processing, plug opening processing or pipetting processing.

Further, when reading with the specimen tag reader unit 5a and the carrier tag reader unit 6a, the central controller 33 checks whether or not processing items other than the preset groups, for example, specimen pipetting volume and analysis items are contained in the read specimen tags. If there exist such processing items other than the preset groups, the central controller 33 sets a command code to the specific controller forming a pair with the specific specimen processing unit which is determined to process such non preset processing item other than the preset groups for requesting inquiries of processing information with regard to such carrier tag.

When a carrier tag of a specimen rack mounting specimen containers having such non preset items is read by the carrier tag reader unit 57, 58 or 59, the specific unit controller which recognizes such carrier tag issues an inquiry to the central controller 33 based on the above mentioned requesting command code. In response to the inquiry, the central controller 33 transmits detailed and specific processing information with regard to the concerned specimen which is read in advance via the communication cable. The specific unit controller which has received such information controls the concerned specific specimen processing unit so as to perform the non preset processing item.

Figure 3:
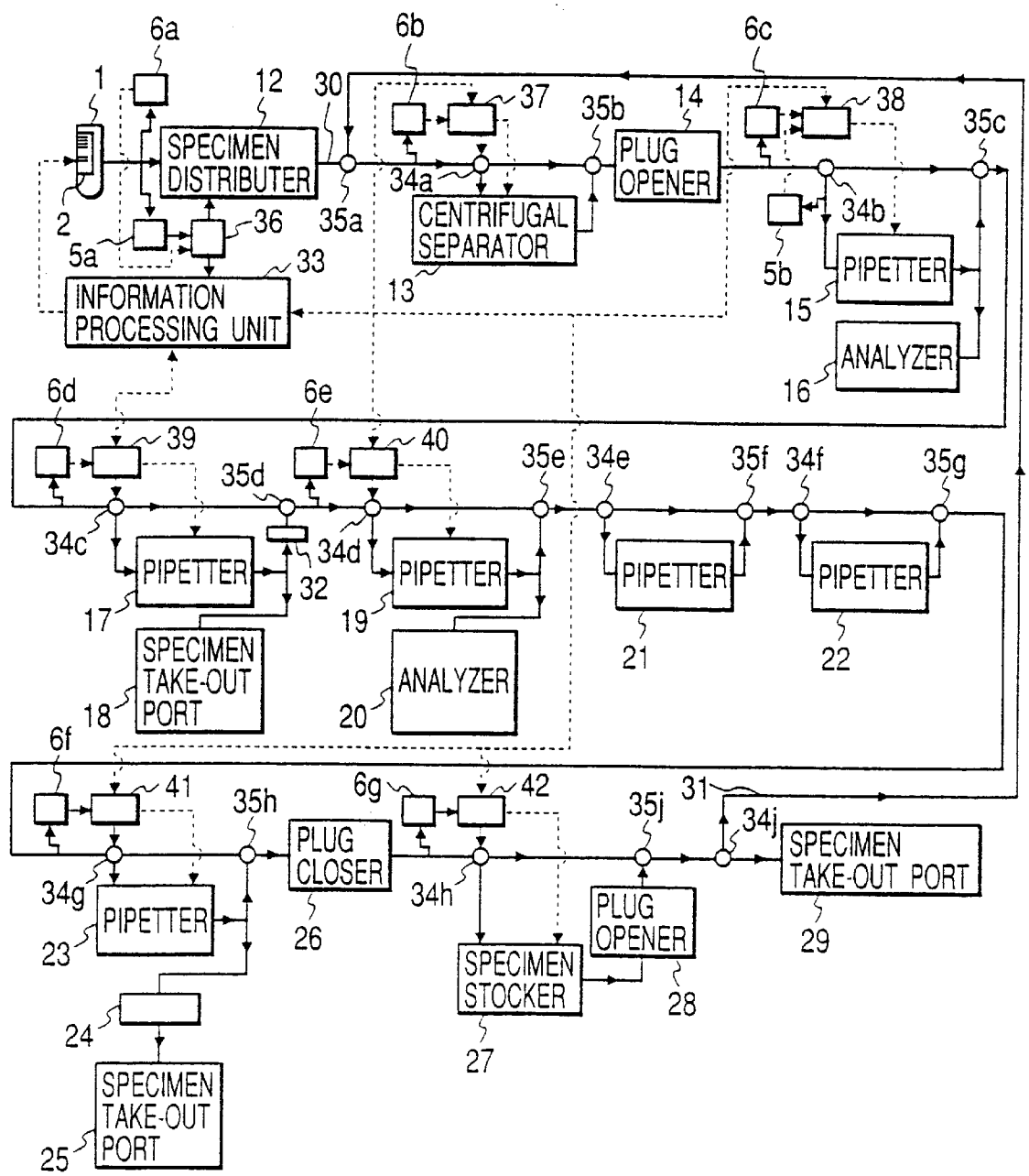
FIG. 3 is a block diagram of another specimen processing system according to the present invention in which a large number of specimen processing devices are disposed, and a view for explaining a specimen processing function according to the present invention.

FIG. 3 shows an example in which a large number of specimen processing devices are arranged along the transportation line as well as a specimen distributer unit is further added. The specimen container 1 on which the specimen tag 2 is adhered is hanged at the supply unit like the supply unit 7 in FIG. 1 under a condition that the specimen container 1 is held on a specimen supporting member functioning as the specimen carrier.

The specimen processing system comprises a specimen distributer 12 which replaces specimen containers 1, each containing specimen such as blood and urine, onto respective new specimen supports 3 depending on their processing contents such as inspection and pipetting, and the system further comprises, specimen tag readers 5a and 5b such as a barcode reader which are designed to read specimen tags 2 adhered on the respective specimen containers 1 mounted on the specimen supports 3 before the replacement, and carrier tag readers 6a through 6g which are designed to read carrier tags 4 adhered on the respective specimen supports 3. On the specimen tag 2, regions for filling-in information, for example, code number representing a group of processing items necessary for the specimen concerned and being set in advance (one processing item group represents one necessary specimen processing item or a series of typical specimen processing items for one specimen concerned), and when there are other processing items than those identified by the code number, information representing necessity or unnecessity of inquiries for further processings, are provided, and the corresponding information is filled in the respective regions concerned.

The above specimen processing system further comprises a transferring line 30 which is designed to transfer the specimen supports 3 after the replacement of the specimen containers 1, a centrifugal separator 13 which centrifuges the specimen under the condition contained in the specimen container 1, a plug opener 14 which pulls out the plug of the specimen container 1, pipetting units 15, 17, 19, 21, 22 and 23 which are designed to pipet the mother specimen in the specimen container 1 centrifuged by the centrifugal separator 13 into a daughter specimen container 1a which is prepared for every aimed inspection and analysis units 16 and 20 which designed to analyze the specimen (hereinbelow called as a daughter specimen) which has been pipetted by the pipetting units 15 and 19.

The specimen processing system, still further, comprises a tag adhering unit 24 which is designed to adhere a daughter specimen tag for the daughter specimen container 1b containing the remaining daughter specimen after pipetting by the pipetting units 23, a specimen take-out port 25 which is designed to take-out the daughter specimen container 1b therefrom, another specimen take-out port 18 which is designed to take-out depending on necessity the specimen container (hereinbelow called as a mother specimen container) 1 after completing pipetting by the pipetting unit 17, a plug closer 26 which is designed to close the plug for the daughter specimen container 1c for preserving the pipetted daughter specimen, a specimen stocker or standing-by unit 27 which is designed to stand by temporarily the plug closed daughter specimen container 1c, another plug opener 28 which is designed to open the plug for the daughter specimen container 1c for reprocessing the standing-by daughter specimen, a return line 31 which is designed to return the mother specimen container 1 or the daughter specimen container 1c to the top portion of the transferring line 30 for reprocessing the same, a specimen take-out port 29 which is designed to take out the mother specimen container 1 and the daughter specimen containers 1a and 1c at the end of the transferring line 30, branching means 34a through 34j which are designed to branch the specimen supports 3 carrying the specimen containers depending on the destination thereof, joining means 35a through 35j which are designed to join the specimen supports 3 depending on the destination thereof, processing control units 37 through 42 which are provided for the respective processing units and are designed to perform the control therefor, and an information processing unit or a central controller 33 which is designed to perform entire control and management of the specimen processing and inspection system.

Now, the operation of the above explained specimen processing and inspection system shown in FIG. 3 will be explained.

The specimen distributer 12 moves specimen supporting members introduced into the specimen supply unit and empty specimen supporting members with no specimen containers toward a replacement station.

The specimen distributer 12 classifies and replaces the specimen containers 1 so that the specimen containers 1 having a same processing item group are mounted and supported on a common empty specimen support 3, on which a specific carrier tag 4 is to be adhered in advance.

The code number determined by coding in advance a plurality of groups of processing items of the specimen and written on respective specimen tags 2 is read by the specimen tag reader 5a, and the read code number is collated with a variety of code numbers which are set in advance in the processing control unit 36 or the central controller 33, and the respective specimen containers 1 which were classified by the specimen distributer 12 are distributed under the control of the processing control unit 36 for the specimen distributer 12 to corresponding specimen supports 3 (destination of distributed specimen containers) which are respectively assigned to respective groups of processing items for the specimens which are set in advance. In the example in FIG. 3, the combination of the central controller 33 and the control unit 36 for the specimen distributer 12 functions as the information managing and control unit.

According to the present embodiment including the control unit 36, necessity of inquiring the information relating to the destination for every specimen container 1 to the information processing unit 33 is eliminated, therefore, even in a specimen processing system having many number of specimen processing units, load for processing information and communication relating to the classification and distribution of the specimens will not be increased.

Subsequently, respective specimen supports 3 mounting specimen containers 1 are transferred through the transferring line 30 in order to process the specimens contained in the respective specimen containers 1 or the specimen containers themselves. The transferred specimen supports 3 are managed while pairing the relationship with the specimen containers 1 mounted and supported thereon. Namely, the processing control unit 36 grasps a corresponding relationship between the carrier tag code of the specimen support 3, and the grouped combination of processing items for their specimens in the specimen containers 1 mounted and supported thereon based on the information on the specimen tags 2 of respective specimen containers 1 which is read by the specimen tag reader 5a during the distribution processing and based on the information on the carrier tags (on which specific number for every specimen support is indicated) 4 of respective specimen supports 3 which are read by the carrier tag reader 6a, and the grasped combined relationship is registered as management information in the information processing unit 33. Thereafter, the information processing unit 33 sets this management information in the respective specimen processing units and/or their processing control units. The information indicating the relationship between the specimen supports and the group of processing items may be set in advance through an off line processing.

The specimen supports 3 which are transferred through the transferring line 30 are branched, if the group of processing items having the corresponding relationship designates centrifugal separation, by the branching means 34a so as to be transferred to the centrifugal separator 13. The specimen support 3 branched toward the centrifugal separator 13 is transferred into the centrifugal separator 13 and the centrifugal separation is performed for the respective specimens. Since the respective specimen containers 1 mounted on the specimen support 3 are grouped which necessitate centrifugal separation depending on their code number relating to centrifugal separation filled in in advance on their specimen tags 2 and are distributed and mounted on a same specimen support 3, the necessity or unnecessity of centrifugal separation for their specimens can be determined by reading the carrier tag 4 on the specimen support 3 with the carrier tag reader 6b and by collating and discriminating the management information set in advance in the processing control unit 37 from the information processing unit 33.

According to the present embodiment, whether the centrifugal separation is to be performed is determined according to the information read from the carrier tag 4 on the specimen support 3 and according to the management information (including code number) set in advance in the processing control unit 37 or the centrifugal separator 13 as a group of processing items for the specimen containers 1 mounted on the specimen support 3, therefore, the centrifugal separation processing for the respective specimens can be performed without inquiring necessity or unnecessity thereof for every specimen container 1 to the information processing unit 33.

The specimen support 3, of which specimens in the respective specimen containers 1 are subjected to and completed of centrifugal separation and are discharged from the centrifugal separator 13, is transferred through the transferring line 30 to the plug opener 14 which opens the plug of the specimen container 1 prior to performing the pipetting processing of the specimens. According to the present embodiment, the plug opener 14 can judge whether the plug opening processing is to be performed based on the information set in the plug opener 14 in a form of code number, and can perform the corresponding processing without inquiring the necessity or unnecessity for every specimen container 1 to the information processing unit 33. Therefore, even in this operation, the processing of information and communication relating to the necessity or unnecessity of plug opening for every specimen container 1 is eliminated which was necessitated until now.

As will be appreciated from the above, the specimen support 3 mounting the specimen containers 1 for which the centrifugal separation and plug opening processing have been completed is further transferred through the transferring line 30 to read the carrier tag 4 by the carrier tag reader 6c, and is branched by the branching means 34b so as to carry the same to the pipetting unit 15. In view of an urgent pipetting processing, the pipetting unit 15 is provided with a specimen receiving port and the specimen tag reader 5b for a newly introduced specimen container 1 at the specimen receiving port, and the information of the carrier tag 4 read by the carrier tag reader 6c and the information of the newly mounted specimen container 1 read by the specimen tag reader 5b are paired (combination of the specimen container 1 and the specimen support 3) and are reregistered in the information processing unit 33.

According to the present embodiment, the information of the respective specimen containers 1 is already written on the respective specimen tags 2 as the coded group of processing items for every specimen support 3 mounting the same and is recognized as the management information by the processing device control unit 38, therefore, the conventional inquiries to the information processing unit 33 required every time when the specimen container 1 (specimen support 3) passes the tag reader is eliminated and a pipetting can be performed automatically according to the pipetting method set in advance in the pipetting unit 15. The specimen support 3 may mount a specimen container having other processing items than the group of processing items set in advance, only in such instance the pipetting information is inquired to the information processing unit 33. Accordingly, even when the number of the specimen containers (specimen supports) is increased, the amount of information and communication with the information processing unit 33 changes slightly, which eliminates the necessity of a complex and large scaled communication system.

The specimen support 3, on which is mounted the mother specimen container 1 having subjected to the pipetting at the pipetting unit 15, is transferred through the transferring line 30 to the subsequent specimen processing unit.

Further, the daughter specimen container 1a containing the daughter specimen pipetted at the pipetting unit 15 is mounted and supported on another specimen support 3 than that of the mother specimen, however, like the mother specimen container 1, the pipetted daughter specimen (daughter specimen container 1a) and the specimen support 3 are correlated according to the specimen tag 2 and the carrier tag 4, and is transferred to the analysis unit 16. With regard to the daughter specimen container 1a transferred to the analysis unit 16 the carrier tag 4 on the specimen support 3 is read by a support tag reader (not shown) provided for the analysis unit 16 to thereby recognize what types of specimens (daughter specimen containers 1a) being mounted on the specimen support 3, and thereafter, a corresponding processing is performed based on the recognized group of processing items for the daughter specimen.

Subsequently, the mother specimen container 1 transferred to the transferring line 30 via the joining means 35c is transferred to the pipetting unit 17 so as to pipet the specimen (for example blood serum) into another daughter specimen container 1b, at the pipetting unit 17 the carrier tag 4 on the specimen support 3 is likely read by the carrier tag reader 6d and a predetermined pipetting processing is performed based on the management information set in advance at the processing device control unit 39. Then, the mother specimen container 1 having completed the pipetting is transferred to the specimen take-out port 18 depending on necessity. With regard to the daughter specimen (containing only the blood serum) pipetted and removed to the other daughter specimen container 1b, a processing device control unit (not shown) of a tag, such as bar code, adhering unit 32 inquires the information about the specimen (specimen container 1) to the information processing unit 33. In response to the inquired information, the bar code labeler 32 performs a processing of issuing a specimen tag 2 on which is written the same information as that of the mother specimen container 1, namely, attributes of the specimen, code number indicating coded group of processing items, information of inquiring necessity or unnecessity on the existence of non-coded processing items, and adhering the same on the daughter specimen container 1b and then send out the same toward the transferring line 30.

In the same manner as above, at the pipetting unit 19 a pipetting processing of the specimen from the daughter specimen container 1b to another daughter specimen container 1c is performed for effecting analysis at the on-line use analysis unit 20, and at the pipetting units 21 and 22 (respective carrier tag readers and processing device control units are not shown) for off-line use analysis units (not shown) and at the pipetting unit 23 for a manual inspection use, other pipetting processings are performed, thereafter, remained daughter specimen, after the plug for the specimen container 1 is closed with the plug closer 26, is preserved temporarily in the specimen stocker 27.

The specimen preserved in the specimen stocker 27 can be freely delivered from the specimen stocker 27 depending on necessity. When it is required to reprocess the preserved specimen, the plug of the specimen container 1c is opened by the plug opener 28, thereafter, the information of the specimen support 3 is read by a carrier tag reader (not shown) to recognize the type of the specimen mounted on the specimen support 3, and the specimen container 1c is transferred through the reprocessing line 31 to the top of the transferring line 30 so as to carry out the required reprocessing.

When no processings are required or when all of the required processings have been completed properly, the concerned specimen container 1 is delivered to the specimen take-out port 29 and stored.

Because of the limited information writing-in space on the specimen tag 2 to be attached on the specimen container, when there are many processing items to be performed at the respective specimen processing units and other processings (processing items) than those defined by code numbers (groups of processing items) set in advance are required, a specific code number is set which indicates necessity or unnecessity of inquiring processing contents to the information processing unit 33, if required.

According to the specimen processing system representing the one embodiment shown in FIG. 3 of the present invention as have been explained above, a code corresponding to a predetermined group of processing items is filled in on specimen tags 2 adhered to respective specimen containers 1, the respective specimen processing units disposed along the transferring line 30 at first classify the specimen containers 1 according to the code corresponding to the predetermined group of processing items to distribute and mount the same onto concerned specimen supports 3, and the mounting specimen support 3 and the group of processing items of the mounted specimen containers 1 are correlated, thereby, the respective specimen processing units can perform the necessary processings for the respective specimens after recognizing the carrier tags 4 attached on the specimen supports 3 without communicating the processing information with the information processing unit 33 every time when the processings are required, the processing amount of communication with regard to processing information between the respective specimen processing units and the information processing unit can be reduced.

With such specimen processing system, in particular, in a specimen processing system having many number of specimens and the specimen processing units the processing amount of information and communication between the information processing unit 33 and the respective specimen processing units is reduced and the specimen processing speed is improved. Further, from another point of view, even in a large scale specimen processing system a simple communication system can be employed which can reduce the cost of such system.

What is claimed is:

1. A specimen processing system comprising a specimen carrier carrying specimen containers each being capable of containing specimen, a transportation line for transportating the specimen carrier and a plurality of specimen processing devices arranged along the transportation line, further comprising specimen tags each attached on the outer wall of the respective specimen containers and including a code representing specimen number and a group code representing one of grouped combinations of processing items performed by at least one of the plurality of specimen processing devices for the specimen contained in the concerned specimen container;

identifiably coded carrier tags each formed on the specimen carrier;

a specimen tag reader for reading the specimen tags prior to transporting the specimen carrier toward the plurality of specimen processing devices;

a first carrier tag reader for reading the carrier tag prior to transporting the specimen carrier toward the plurality of specimen processing devices;

second carrier tag readers arranged for each of the plurality of specimen processing devices;

processing device controllers each forming a pair with each of the respective specimen processing devices and for receiving information read from the concerned second carrier tag reader; and an information managing and controlling unit which registers corresponding relationship between the carrier tag and the group code for individual specimen carriers based on the read results of the specimen tags by the specimen tag reader and of the carrier tags by the first carrier tag reader, wherein each of the processing device controllers receives the registered corresponding relationship from the information managing and controlling unit and manages the carrier tag relating to the specimen processing device which forms a pair with the concerned processing device controller.

2. A specimen processing system according to claim 1, wherein each of the specimen processing devices, when carrier tag read by the concerned second carrier tag reader contains the group code corresponding to the processing items concerned to the specimen processing device, performs the processing of concerned processing items for the specimen container or the specimen on the specimen carrier bearing the read carrier tag.

3. A specimen processing system according to claim 1, wherein the processing items contained in the identifiable groups are selected from a group of centrifugal separation, plug opening, specimen pipetting, specimen analysis, plug closing and temporarily standing-by.

4. A specimen processing system according to claim 1, wherein when a processing item is included which does not correspond to any of preset groups among specimen tags read by the specimen tag reader, the information managing and controlling unit sets an inquiry request command to a specific processing device controller of a concerned specific specimen processing device which is determined to perform the processing of the non corresponding processing items, and when the specific processing device controller recognizes the concerned carrier tag having the corresponding relationship with the non corresponding processing items, the specific processing device controller inquires processing information to the information managing and controlling unit and controls based on the processing information received from the information managing and controlling unit the concerned specific specimen processing device so as to perform the non corresponding processing items.

5. A specimen processing system according to claim 1, wherein the specimen processing system is further provided with a specimen distributing device in which, after reading tags with the specimen tag reader and the first carrier tag reader, a plurality of specimen containers bearing a same group code are mounted on a common specimen carrier and a specimen carrier completing the mounting of the plurality of specimen containers is supplied to the transportation line.

\* \* \* \* \*